US010161877B2

(12) United States Patent
Lin et al.

(10) Patent No.: US 10,161,877 B2
(45) Date of Patent: Dec. 25, 2018

(54) OPTICAL DETECTION SYSTEM

(71) Applicant: DELTA ELECTRONICS, INC., Taoyuan (TW)

(72) Inventors: Ming-Shu Lin, Taoyuan (TW);
Ying-Ting Chen, Taoyuan (TW);
Wang-Chu Chen, Taoyuan (TW);
Ching-Yu Chang, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 0 days.

(21) Appl. No.: 15/701,746

(22) Filed: Sep. 12, 2017

(65) Prior Publication Data

US 2018/0080879 A1     Mar. 22, 2018

Related U.S. Application Data

(60) Provisional application No. 62/397,609, filed on Sep. 21, 2016.

(30) Foreign Application Priority Data

Apr. 7, 2017   (CN) .......................... 2017 1 0223474

(51) Int. Cl.
*G01N 31/22*  (2006.01)
*G01N 21/78*  (2006.01)
*G01N 21/77*  (2006.01)

(52) U.S. Cl.
CPC ..... *G01N 21/78* (2013.01); *G01N 2021/7759* (2013.01); *G01N 2021/7783* (2013.01); *G01N 2201/062* (2013.01); *G01N 2201/12* (2013.01)

(58) Field of Classification Search
CPC ............... G01N 21/78; G01N 2201/12; G01N 2021/7759; G01N 2201/062; G01N 2021/7783
See application file for complete search history.

(56) References Cited

U.S. PATENT DOCUMENTS 6,267,722 B1 *   7/2001  Anderson ............ G01N 21/474
                                                        600/300
7,044,919 B1 *   5/2006  Catt ................... A61B 10/0012
                                                        436/65

(Continued)

FOREIGN PATENT DOCUMENTS

TW    201500728    1/2015
TW    201510522    3/2015

*Primary Examiner* — Dennis White
(74) *Attorney, Agent, or Firm* — Muncy, Geissler, Olds & Lowe, P.C.

(57) ABSTRACT

An optical detection system includes a light emitting module, a test strip and a receiving module. The light emitting module includes a light source and a first light shielding unit. The first light shielding unit has a first aperture corresponding to the light source. The test strip includes a cassette and a light permeable test paper. The cassette has a first window, a second window and a sample opening disposed on one surface of the cassette. The first and second windows are disposed corresponding to each other and located on opposite sides of the cassette, respectively. The light permeable test paper is disposed in the cassette. The receiving module includes a second light shielding unit and a photo sensor. The second light shielding unit has a second aperture corresponding to the second window. The photo sensor receives the light beam from the light source and outputs a measurement signal.

15 Claims, 7 Drawing Sheets

(56) References Cited

U.S. PATENT DOCUMENTS

2013/0011928 A1 1/2013 Gao
2014/0318986 A1 10/2014 Elder et al.

* cited by examiner

OPTICAL DETECTION SYSTEM

CROSS REFERENCE TO RELATED APPLICATIONS

The non-provisional patent application claims priority to U.S. provisional patent application with Ser. No. 62/397,609, filed on Sep. 21, 2016. This and all other extrinsic materials discussed herein are incorporated by reference in their entirety.

This Non-provisional application claims priority under 35 U.S.C. § 119(a) on Patent Application No(s). 201710223474.6, filed in People's Republic of China on Apr. 7, 2017, the entire contents of which are hereby incorporated by reference.

BACKGROUND OF THE INVENTION

Field of Invention

The present disclosure relates to an optical detection system for detecting a test strip.

Related Art

The existing lateral flow assay (LFA) is convenience in use and has well-developed manufacturing processes, so it is widely applied for rapid screening tests. Colloid gold method is the most popular category of LFA tests. In, the colloid gold method, the gold nanoparticles will aggregate at the control and test bands after reaction. The test results can be determined by human eyes, an optical detection or an image analysis. However, during visual inspection, the interpretation can be varied by different users. Besides, some weak reactions, which have nonobvious colorations, may cause the improper interpretation by the users. The reflective optical detection which is applied for most commercial rapid test reader can only detect the color change on the surface of the test strip, but it cannot detect out the color change hidden inside the fibers of the test strip. Moreover, the reflective optical signal can be easily affected by the distance between strip surface and optical sensor. A sophisticated design is required to stabilize the light path, which causes additional design and fabrication cost.

In addition, the layout of control and test lines on a test strip might be varied according to different applications. Moreover, it is a challenge to fabricate the control and test lines at a specific position for the fixed optical sensor of a reader. The CMOS image capturing device can retrieve the image of the rapid test via camera and then select a specific reaction region by image analyzing technology for quantization based on the color or brightness/darkness of the selected region. However, longer focal length and higher hardware specification do not meet the requirement of an affordable portable device. Therefore, it is an important subject to improve the convenience and sensitivity of the detection device.

SUMMARY OF THE INVENTION

In view of the foregoing, an objective of the disclosure is to provide a transmission optical detection system that can decrease the design complexity, increase the detection reliability, and improve the detection sensitivity by detecting the reaction signal hidden inside a test strip.

To achieve the above objective, the present disclosure provides an optical detection system including a light emitting module, a test strip and a receiving module. The light emitting module includes a light source and a first light shielding unit. The light source provides a light beam. The first light shielding unit has a first aperture, which is disposed corresponding to the light source. The test strip includes a cassette and a light permeable test paper. The cassette has a first window, a second window and a sample opening. The sample opening is disposed on a surface of the cassette. The first window and the second window are disposed corresponding to each other and located on opposite sides of the cassette, respectively, and the first window is disposed corresponding to the first aperture. The light permeable test paper is disposed in the cassette. The receiving module includes a second light shielding unit and a photo sensor. The second light shielding unit has a second aperture, which is disposed corresponding to the second window. The photo sensor receives the light beam and outputs a measurement signal. The light beam travels through the first aperture of the first light shielding unit, the first window, the light permeable test paper, the second window and the second aperture of the second light shielding unit in order.

In one embodiment, the light permeable test paper includes at least a test band and a control band, and the test band and the control band are distributed in an intersection region of vertical projections of the first window and the second window on the light permeable test paper.

In one embodiment, a diameter of the first aperture is less than or equal to a width of the test band and a width of the control band.

In one embodiment, a diameter of the second aperture is less than or equal to a diameter of the first aperture.

In one embodiment, a diameter of the first aperture is between 0.1 mm and 5.0 mm.

In one embodiment, the light source is a light-emitting diode, the light permeable test paper includes a coloration material, and at least a wavelength of the light-emitting diode is an absorption wavelength of the coloration material.

In one embodiment, the light source, the first aperture, the second aperture and the photo sensor together form an optical detection path, and the optical detection path is substantially perpendicular to the test strip.

In one embodiment, the optical detection system further includes a strip moving carrier for fixing the test strip and linearly moving the test strip along a long axis of the first window, and the light beam irradiates a part of the cassette and the first window along the long axis.

In one embodiment, the strip moving carrier is an auto driving device or a manual driving device.

In one embodiment, the auto driving device is driven by a motor configured with a gearing module, and the gearing module includes a sliding track, a screw rod, a gearwheel or a belt.

In one embodiment, the manual driving device includes a sliding bulk and a sliding slot for linearly moving the test strip by hands or springs.

In one embodiment, the optical detection system further includes a signal analyzing module including a signal analyzing unit and a signal computing unit. The signal analyzing unit receives the measurement signal and retrieves a parameter from the measurement signal. The parameter is a background signal parameter, a control signal parameter, a test signal parameter, or a first window time parameter. The signal computing unit computes a concentration of a specific substance in a given sample based on at least one of the parameters.

In one embodiment, the optical detection system measures a detection signal hidden in fibers of the light permeable test paper through a transmission optical detection path.

As mentioned above, the optical detection system of this disclosure can measure a detection signal hidden in fibers of the light permeable test paper through a transmission optical detection path so as to increase the intensity of the detection signal. The optical detection path has a scan design for scanning the blank region, the test band and the control band in the first window in order along the long axis direction of the first window of the test strip. Thus, the number of photo sensors can be reduced, thereby reducing the design complexity, increasing the flexibility for configuring different numbers of the test bands on the test strip, and decreasing line accurate requirement of the test band and control band. Moreover, the cooperation of the first aperture and the second aperture can increase the reliability of the measurement signal, enhance the noise ratio of the measurement signal, and improve the convenience and sensitive of the detection device.

BRIEF DESCRIPTION OF THE DRAWINGS

The present disclosure will become more fully understood from the subsequent detailed description and accompanying drawings, which are given by way of illustration only, and thus are not limitative of the present disclosure, and wherein.

DETAILED DESCRIPTION OF THE DISCLOSURE

The present disclosure will be apparent from the following detailed description, which proceeds with reference to the accompanying drawings, wherein the same references relate to the same elements.

Figure 1:
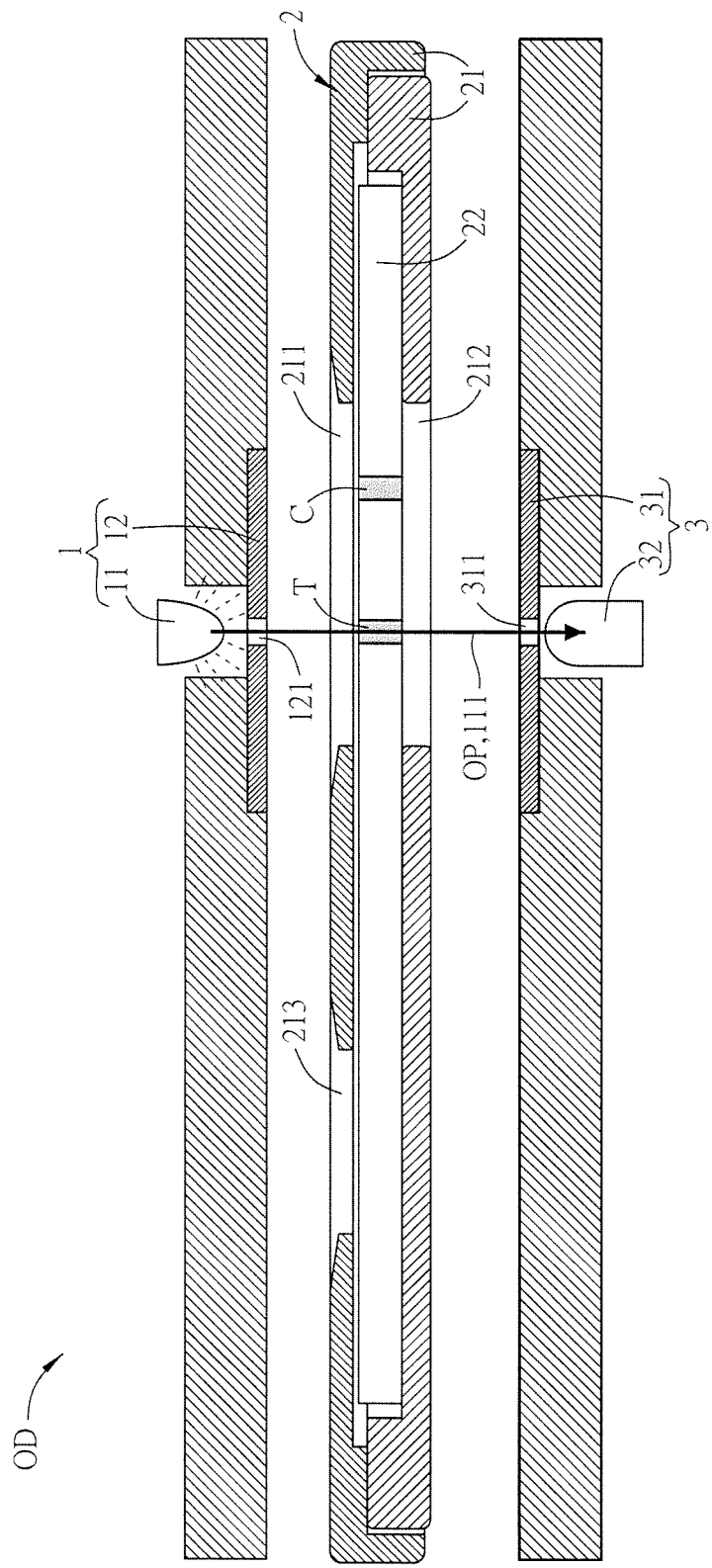
FIG. 1 is a schematic diagram showing an optical detection system according to an embodiment of the disclosure.
Figure 2:
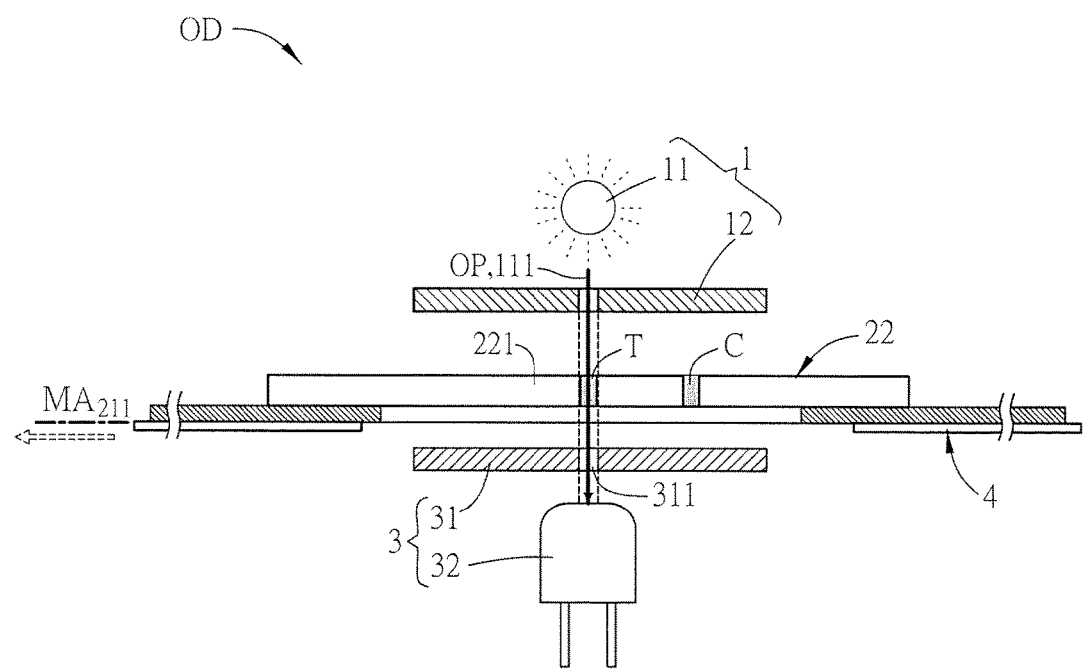
FIG. 2 is a schematic diagram showing an optical detection path according to an embodiment of the disclosure.
Figure 3A:
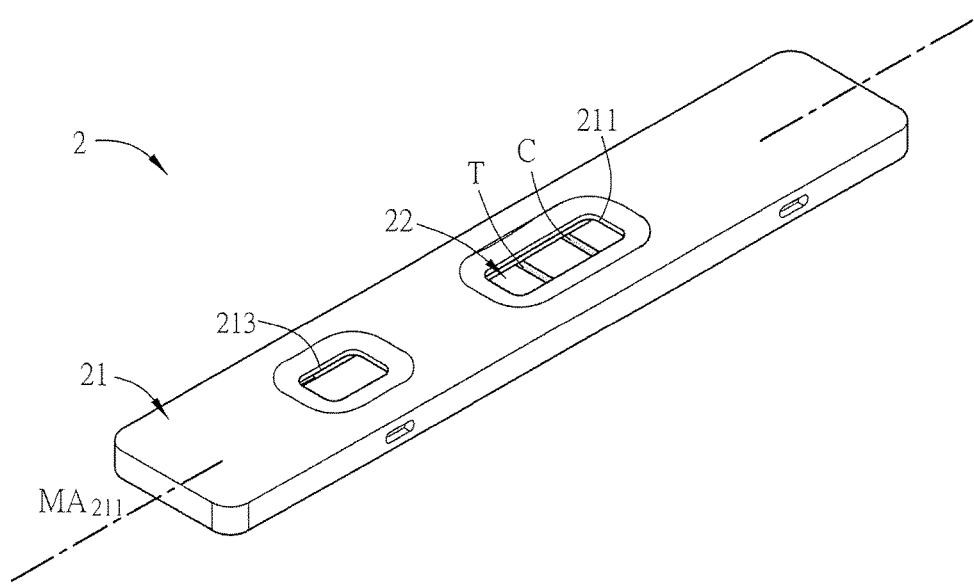
FIG. 3A is a perspective diagram of a test strip according to an embodiment of the disclosure.
Figure 3B:
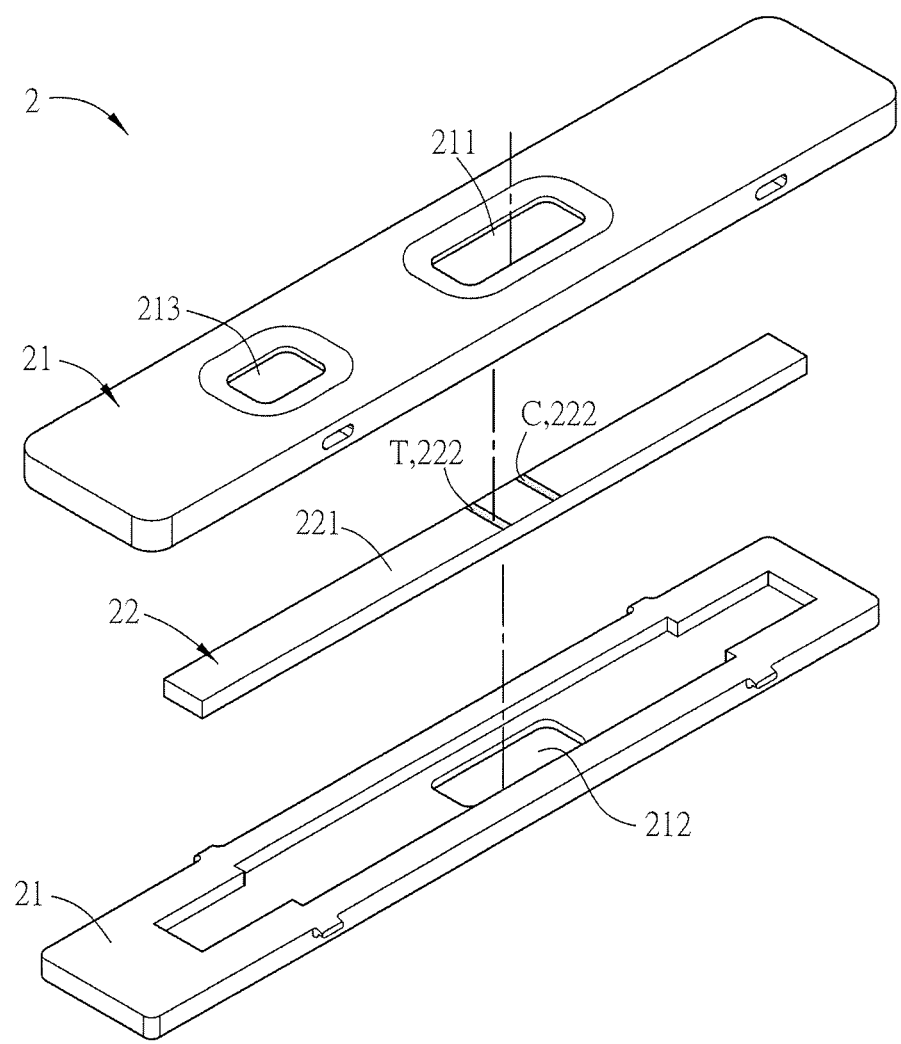
FIG. 3B is an exploded view of the test strip of FIG. 3A.

FIG. 1 is a schematic diagram showing an optical detection system according to an embodiment of the disclosure. FIG. 2 is a schematic diagram showing an optical detection path according to an embodiment of the disclosure, and the cassette of the test strip is omitted in FIG. 2. FIG. 3A is a perspective diagram of a test strip according to an embodiment of the disclosure, and FIG. 3B is an exploded view of the test strip of FIG. 3A.

Referring to FIGS. 1, 2, 3A and 3B, an optical detection system OD of this disclosure includes a light emitting module 1, a test strip 2, and a receiving module 3. The light emitting module 1 includes a light source 11 and a first light shielding unit 12. The light source 11 provides a light beam 111. The first light shielding unit 12 has a first aperture 121, which is disposed corresponding to the light source 11. The light beam 111 passes through the first light shielding unit 12 via the first aperture 121.

The test strip 2 includes a cassette 21 and a light permeable test paper 22. The cassette 21 has a first window 211, a second window 212, and a sample opening 213. The sample opening 213 is disposed on a surface of the cassette 21. The first window 211 and the second window 212 are disposed corresponding to each other and located on opposite sides of the cassette 21, respectively. The first window 211 is disposed corresponding to the first aperture 121. The light permeable test paper 22 is disposed in the cassette 21. The light beam 111 outputted from the first light shielding unit 12 can pass through the first window 211 and the light permeable test paper 22 in order, and then be outputted from the test strip 2 via the second window 212.

The receiving module 3 includes a second light shielding unit 31 and a photo sensor 32. The second light shielding unit 31 has a second aperture 311, which is disposed corresponding to the second window 212. The light beam 111 outputted from the test strip 2 can enter the second light shielding unit 31 via the second aperture 311, and the photo sensor 32 receives the light beam and outputs a measurement signal accordingly. The light beam 111 outputted from the first aperture 121 of the first light shielding unit 12 can travel through the first window 211, the light permeable test paper 22 and the second window 212 in order, and then enter the second light shielding unit 31 via the second aperture 311.

The optical detection system of this disclosure can measure a detection signal hidden in fibers of the light permeable test paper through a transmission optical detection path. The light beam travels through the first aperture of the first light shielding unit, the first window, the light permeable test paper, the second window and the second aperture of the second light shielding unit in order. In this embodiment, the light source 11, the first aperture 121, the second aperture 311 and the photo sensor 32 can together form an optical detection path OP, and the optical detection path OP is substantially perpendicular to the test strip 2. The detection reaction region of the test strip 2 has a hollow design, so that the detection strip 2 has a first window 211 and a second window 212 disposed corresponding to each other. The light permeable test paper 22 includes at least one test band T and a control band C, which are distributed in an intersection region of vertical projections of the first window 211 and the second window 212 on the light permeable test paper 22. In other words, the test band T and the control band C are distributed on the light permeable test paper 22, so that the light beam 111 outputted from the light emitting module 1 can pass through the first window 211, the test band T or the control band C of the light permeable test paper 22, and the second window 212. After leaving the test strip 2 via the second window 212, the light beam 111 carrying the detection signal of the test band T or the control band C can be received by the receiving module 3.

In this embodiment, the diameter of the first aperture 121 is between 0.1 mm and 5.0 mm. Since the diameter of the first aperture 121 is less than or equal to the width of the test band T and the width of the control band C, the width of the light beam 111 is less than the width of the test band T and the width of the control band C when the light beam 111 passes through the test band T or the control band C. In addition, since the diameter of the second aperture 311 is less than the diameter of the first aperture 121, the photo sensor 32 can filter away the redundant noise as receiving the light beam 111, thereby increasing the reliability of the measurement signal.

Based on the transmission optical detection path design, the positions of the light source and the photo sensor are fixed, so that the detection signal is not affected by the distance change between the light permeable test paper and the photo sensor easily. Besides, since the diameter of the first aperture is less than or equal to the width of the test band and the width of the control band and the diameter of the second aperture is less than or equal to the diameter of the first aperture, the issue of uneven light intensity can be minimized. Thus, a single photo sensor is enough for the detection and the additional optical diffuser is not needed. This configuration can make the structure of the detection device simpler and can simplify the calibration procedure.

In this embodiment, the optical detection system OD further includes a strip moving carrier 4 for fixing the test strip 2 and linearly moving the test strip 2 along a long axis MA211 of the first window 211, and the light beam irradiates a part of the cassette and the first window along the long axis. Accordingly, the light beam can travel along the long axis MA211 to irradiate a part of the cassette 21 and the first window 211. In more detailed, the strip moving carrier 4 can move the test strip 2, so that the test strip 2 has a linear move with respect to the fixed optical detection path OP. Thus, the optical detection path OP extends along the long axis MA211 of the first window 211 to pass through a part of the cassette 21, the blank region 221, test band T and control band C of the light permeable test paper 22 in the first window 211, and the blank region 221 of the light permeable test paper 22. After the optical detection path OP leaves the first window 211 and reaches a part of the cassette 21, the strip moving carrier 4 stops moving the test strip 2.

In this embodiment, the strip moving carrier 4 is an auto driving device or a manual driving device. The auto driving device is driven by a motor (not shown), which configured with a gearing module (e.g. a sliding track, a screw rod, a gearwheel or a belt), for linearly moving the test strip 2 along the long axis $MA_{211}$ of the first window 211. The manual driving device includes a sliding bulk and a sliding slot (not shown) for linearly moving the test strip 2 by hands or springs.

In the scanning optical detection path design, the test strip has a linear move with respect to the optical detection path, so that the optical detection path can scan the test band(s) and the control band on the light permeable test paper in order. This configuration can overcome the undesired shifting problem of the photo sensor and the light permeable test paper due to the manufacturing variations and product compatibility. Moreover, it is possible to decrease the accurate requirement for manufacturing the light permeable test paper and provide the flexibility for increasing/decreasing the amount of the test bands.

Figure 4:
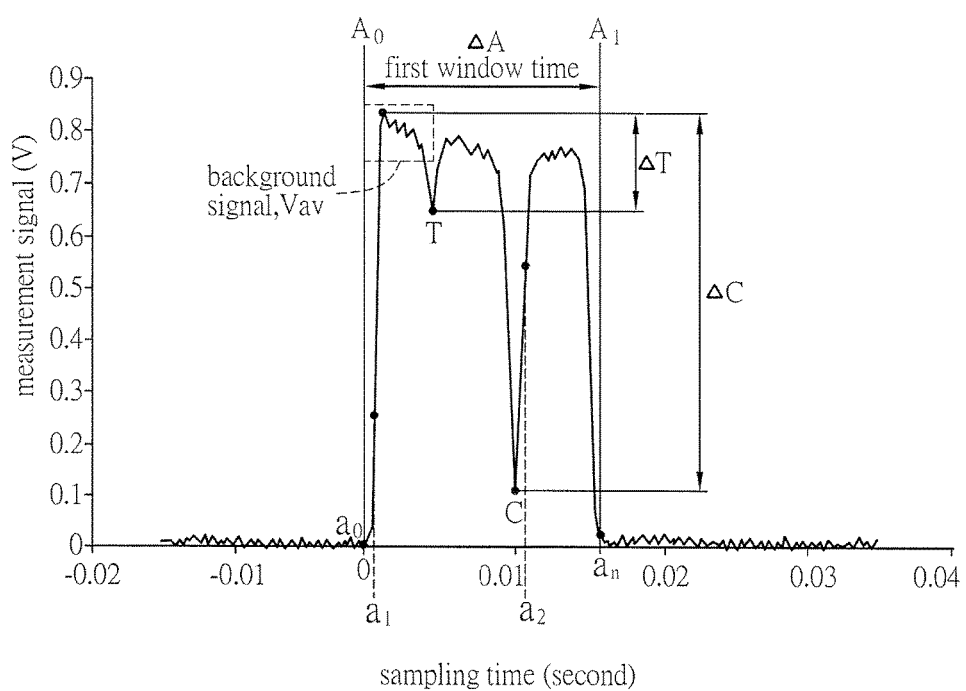
FIG. 4 is a schematic diagram showing the waveforms of the output measurement signal according to an embodiment of the disclosure.
Figure 5:
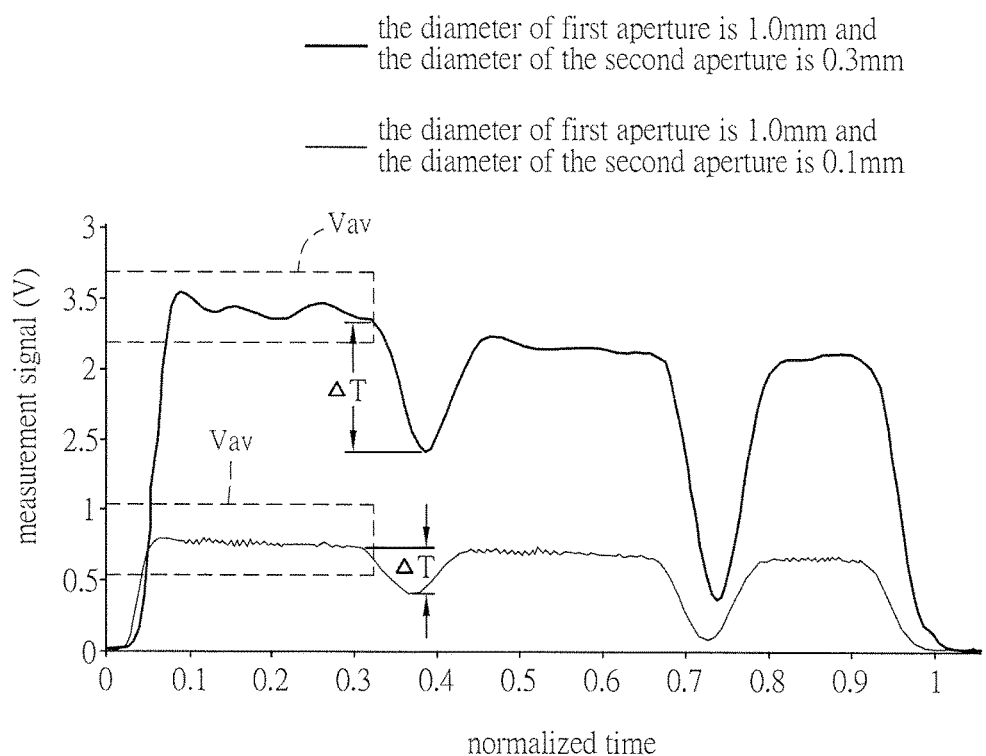
FIG. 5 is a schematic diagram showing the waveforms of the output measurement signal according to another embodiment of the disclosure.
Figure 6:
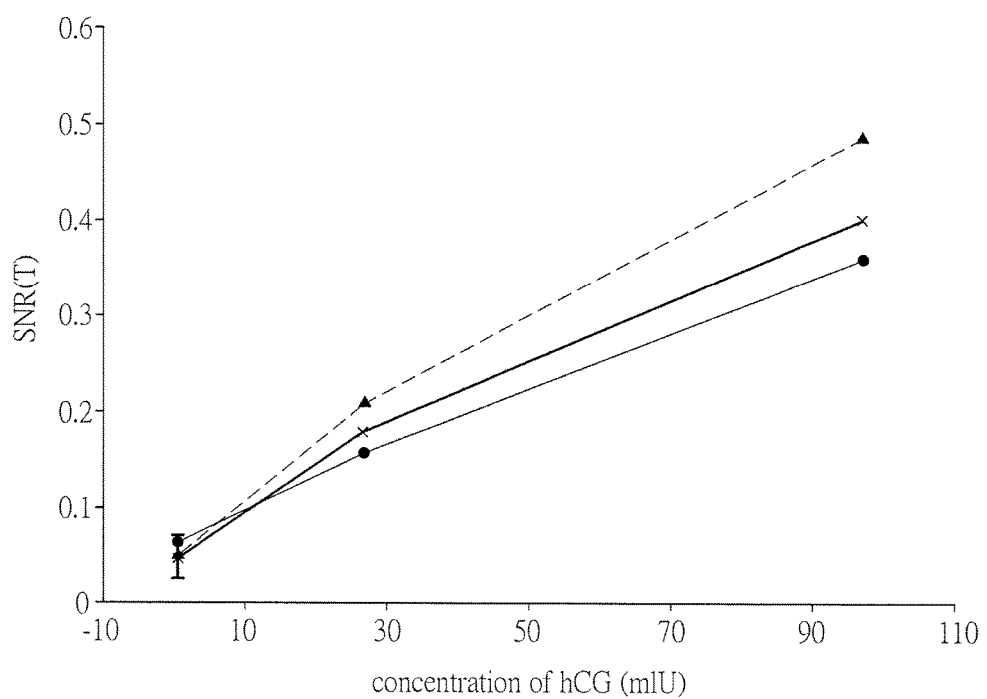
FIG. 6 is a schematic diagram showing the signal noise ratio of the test band according to an embodiment of the disclosure.

FIG. 4 is a schematic diagram showing the waveforms of the output measurement signal according to an embodiment of the disclosure, FIG. 5 is a schematic diagram showing the waveforms of the output measurement signal according to another embodiment of the disclosure, and FIG. 6 is a schematic diagram showing the signal noise ratio of the test band according to an embodiment of the disclosure.

In one embodiment, the light source 11 is a light-emitting diode, and the light permeable test paper 22 includes a coloration material 222. The wavelength of a light emitted from the light-emitting diode is an absorption wavelength of the coloration material 222. The coloration material 222 is coated on the test band T and the control band C of the light permeable test paper 22. When the light beam 111 passes through the test band T or the control band C, a part of the wavelength is absorbed by the coloration material 222, and the light intensity of the light beam 111 is reduced. Then, the photo sensor 32 receives the light beam 111 and output the measurement signal according to the light intensity variations.

In one embodiment, the optical detection system OD further includes a signal analyzing module, which includes a signal analyzing unit and a signal computing unit. The signal analyzing unit receives the measurement signal and outputs a parameter according to the measurement signal. The parameter can be a background signal parameter, a control signal parameter, a test signal parameter, or a first window time ΔA parameter. The signal computing unit computes based on at least one of the parameters and outputs a signal noise ratio.

The operation of the signal analyzing module of this embodiment will be described herein below with reference to FIGS. 4, 5 and 6.

When the optical detection path OP scans the test strip 2 along the long axis $MA_{211}$ of the first window 211, the waveform of the output measurement signal can be obtained as shown in FIG. 4. In FIG. 4, the horizontal axis is the sampling time of the detection of the optical detection path OP, and the vertical axis is the voltage of the measurement signal. Since the cassette 21 of the test strip 2 is made of opaque material, the measurement signal detected by the optical detection path OP is almost zero. As the test strip 2 moves and the optical detection path OP enters the first window 211, the light beam 111 can pass through the blank region 221 of the light-permeable test strip 22, so that the voltage of the measurement signal rapidly increases. At this moment, the sampling time is set as 0. Afterwards, when the optical detection path OP passes through the test band T and the control band C, a part of the wavelength is absorbed by the coloration material 222, so that the light intensity of the light beam 111 is reduced. Thus, two obvious drops of the measurement signal can be obtained for representing the test band signal and the control band signal (points T and C). After the optical detection path OP leaves the first window 211 and the light beam 111 irradiates the cassette 21 of the test strip 2, the measurement signal returns to zero. Then, the entire detection procedure is finished.

In the above detection procedure, the strip moving carrier 4 can be an auto driving device or a manual driving device, and the moving speed of the test strip 2 only relates to the response time of the measurement signal while the drops of the measurement signal (points T and C) are not affected by the moving speed. Thus, the strip moving carrier 4 can be used in the measurement and analyzing.

The details and meanings of some parameters and their values will be defined herein after.

The first window time ΔA is the time period from the light beam 111 entering the first window 211 to the light beam 111 leaving the first window 211.

The background signal is the average value Vav of the measurement signal as the light beam 111 passes through the blank region 221 of the light permeable test paper 22.

The test band signal T is the lowest value of the measurement signal as the light beam 111 passes through the test band T.

The control band signal C is the lowest value of the measurement signal as the light beam 111 passes through the control band C.

$$\Delta T = ABS|\text{background signal} - \text{test band signal}|$$

$$\Delta C = ABS|\text{background signal} - \text{control band signal}|$$

Signal noise ratio of test band SNR(T)=ΔT/background signal

Signal noise ratio of control band SNR(C)=ΔC/background signal

The average value Vav of the measurement signal of the blank region 221 of the light permeable test paper 22 is set as the background signal, and the drops of the measurement signal corresponding to the test band T and the control band C (points T and C) are calculated to obtain the test band signal T and the control band signal C. Then, the difference between the test band signal T and the background signal (ΔT) and the difference between the control band signal C and the background signal (ΔC) are normalized with the background signal so as to obtain the signal noise ratio of the test band SNR(T) and the signal noise ratio of the control band SNR(C).

As shown in FIG. 4, the value of the measurement signal is ranged from 0 to 1. Before the light beam 111 enters the first window 211 and irradiates the cassette 21 of the test strip 2, the light beam 111 is blocked by the cassette, so the light beam 111 is almost not entering the photo sensor 32. Thus, the value of the measurement signal is almost zero. After the light beam 111 enters the first window 211 and irradiates the blank region 221 of the light permeable test paper 22, the light beam 111 is mostly penetrating through the light permeable test paper 22 and entering the photo sensor 32. Thus, the value of the measurement signal is rapidly increased, and the response curve goes up from the point 0. When the detection path passes through the control band C and the test band T, a part of the light beam 111 is absorbed by the coloration material 222, so two obvious drops are generated. After the light beam 111 leaves the first window 211, the light beam 111 is blocked by the cassette 21 again and the value of the measurement signal returns to zero again. The difference between the drop of the control band C and the background signal and the difference between the drop of the test band T and the background signal are calculated to obtain the signal noise ratio of the test band SNR(T) and the signal noise ratio of the control band SNR(C). When the concentrate of the given sample in the test strip 2 increases, the value of the signal noise ratio SNR will rise as the density of the coloration material 222 in the test band T and the control band C increases.

FIG. 5 is a schematic diagram showing the waveforms of the output measurement signal, which can be obtained by studying the effect of different diameters and widths of the first aperture 121 and the second aperture 311 in the optical detection path OP. When the light source 11 of the light emitting module 1 has fixed wavelength and frequency, and the diameter of the first aperture 121 is fixed as 1.0 mm, the second apertures 311 of different sizes (0.1 mm, 0.3 mm) are used to test the hCG (Human Chorionic Gonadotropin) sample (100 mIU) in the test strip 2. Besides, the normalization is applied to the first window time ΔA of the waveform of the output measurement signal.

The calculation of the normalization of the first window time is introduced in the following example, and the details and meanings of some parameters and their values will be defined herein after.

The first window time $\Delta A = A1 - A0$
The time difference $\Delta a_1 = a_1 - a_0$
The time difference $\Delta a_2 = a_2 - a_0$
The time difference $\Delta a_n = a_n - a_0$
Normalizing the first window time = $\Delta a_{1 \sim n}/\Delta A$ As shown in FIG. 4, when the light beam 111 enters the first window 211 and irradiates the blank region 221 of the light permeable test paper 22, the time point that the photo sensor 32 starts to receive the measurement signal is set as the zero point of the time axis $A0$, $a_0$. When the light beam 111 leaves the first window 211, the time point is $A1$. $A1-A0$ is the first window time ΔA. During the first window time, the time values of the measurement signals are $a_1, a_2 \ldots a_n$, which are subtracted by $a_0$ so as to obtain the time differences of the measurement signals $\Delta a_1, \Delta a_2 \ldots \Delta a_n$. The time differences $\Delta a_1, \Delta a_2 \ldots \Delta a_n$ are divided by the first window time ΔA to finish the normalization of the first window time ΔA of the entire measurement signal.

After the normalization of the first window time ΔA of the measurement signal, when the diameter of the first aperture 121 is fixed as 1.0 mm, the level of the measurement signal as the diameter of the second aperture 311 is 0.3 mm will be higher than the level of the measurement signal as the diameter of the second aperture 311 is 0.1 mm. Accordingly, in the optical detection system OD of this embodiment, increasing the diameter of the second aperture 311 can rise the background signal and the measurement signal when the diameter of the first aperture 121 and the light conditions are fixed. As shown in FIG. 5, after analyzing the signal noise ratios SNR(T) of the test band of the above two cases, the curve of the signal noise ratios SNR(T) of the test band as the diameter of the second aperture 311 is 0.1 mm is higher than the curve of the signal noise ratios SNR(T) of the test band as the diameter of the second aperture 311 is 0.3 mm.

As shown in FIG. 5, when the strip moving carrier 4 is a manual driving device for moving the test strip 2, the values of the first window times ΔA in different measurement signals may have variations, but the drop points of the measurement signals of the test band signal T and the control band signal C will be the same after the normalization of the measurement signal. Accordingly, the normalization of the first window time ΔA is benefit to the simplification of the following measurement signal analyzing procedure.

The optical detection system OD is configured with the first aperture 121 and the second aperture 311 for limiting the width of the light beam 111 irradiated on the test strip 2, thereby preventing the background signal other than the test band T and the control band C from entering the photo sensor 32. This design can avoid the measurement signal of the blank region 221 of the light permeable test paper 22 and the measurement signal of the test band T or the control band C of the light permeable test paper 22 from entering the photo sensor 32 simultaneously, thereby preventing the undesired increase of the background signal and the signal noise ratio SNR.

FIG. 6 is a schematic diagram showing the signal noise ratio of the test band according to an embodiment of the disclosure. In this embodiment, the test strip 2 is used to test the hCG (Human Chorionic Gonadotropin) samples of different concentrations (0.25 mIU, 100 mIU), and the signal noise ratio of the test band SNR(T) changes as the different sizes of the first aperture 121 and the second aperture 311 are used. When the diameter of the first aperture 121 is fixed as 0.1 mm, the value of the signal noise ratios SNR(T) of the test band as the diameter of the second aperture 311 is 1.0 mm is higher than the value of the signal noise ratios SNR(T) of the test band as the diameter of the second aperture 311 is 6.0 mm. In addition, when the diameter of the second aperture 311 is fixed as 6.0 mm, the value of the signal noise ratios SNR(T) of the test band as the diameter of the first aperture 121 is 0.1 mm is higher than the value of the signal noise ratios SNR(T) of the test band as the diameter of the first aperture 121 is 1.0 mm. Accordingly, when fixing the diameter of one of the first aperture 121 and the second aperture 311, the value of the signal noise ratio SNR can be increased by reducing the diameter of the other aperture. Moreover, the clear measurement signal waveform and better signal noise ratio value can be obtained by proper cooperation of the first aperture 121 and the second aperture 311. Preferably, the optimum signal noise ratio value can be obtained as the diameter of the first aperture 121 is 0.1 mm and the diameter of the second aperture 311 is 1.0 mm.

As shown in FIG. 6, the concentration of the given sample in the test strip 2 can be calculated by quantifying the value of the signal noise ratio SNR.

As mentioned above, the optical detection system of this disclosure can measure a detection signal hidden in fibers of the light permeable test paper through a transmission optical detection path so as to increase the intensity of the detection signal. The optical detection path has a scan design for scanning the blank region, the test band and the control band in the first window in order along the long axis direction of the first window of the test strip. Thus, the number of photo sensors can be reduced, thereby reducing the design complexity, increasing the flexibility for configuring different numbers of the test bands on the test strip, and decreasing line accurate requirement of the test band and control band.

Moreover, the cooperation of the first aperture and the second aperture in the transmission optical detection path of the optical detection system of the disclosure can increase the reliability of the measurement signal, enhance the noise ratio of the measurement signal, and increase the value of the signal noise ratio SNR of the measurement signal. Accordingly, the limitation of the detection (LOD) of the detection device can be test strip can be reduced, and the convenience and sensitive of the detection device can be improved.

Although the present disclosure has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the present disclosure.

What is claimed is:

1. An optical detection system, comprising:
   a light emitting module, comprising:
      a light source, providing a light beam, and
      a first light shielding unit, having a first aperture, wherein the first aperture is disposed corresponding to the light source;
   a test strip, comprising:
      a cassette, having a first window, a second window and a sample opening, wherein the sample opening is disposed on a surface of the cassette, the first window and the second window are disposed corresponding to each other and located on opposite sides of the cassette, respectively, and the first window is disposed corresponding to the first aperture, and
      a light permeable test paper, disposed in the cassette, wherein the light permeable test paper comprises at least a test band or a control band, and the test band or the control band has a length and a width, and the length is greater than the width; and
   a receiving module, comprising:
      a second light shielding unit, having a second aperture, wherein the second aperture is disposed corresponding to the second window, and
      a photo sensor, receiving the light beam and outputting a measurement signal;
   wherein the light beam travels through the first aperture of the first light shielding unit, the first window, the light permeable test paper, the second window and the second aperture of the second light shielding unit in order, a diameter of the first aperture is less than or equal to the width of the test band and the width of the control band so that the irradiation range of the light beam passing through the test band or the control band is limited within the width of the test band or the width of the control band.

2. The optical detection system of claim 1, wherein the test band and the control band are distributed in an intersection region of vertical projections of the first window and the second window on the light permeable test paper.

3. The optical detection system of claim 2, wherein a diameter of the first aperture is less than or equal to a width of the test band and a width of the control band.

4. The optical detection system of claim 1, wherein the diameter of the first aperture is between 0.1 mm and 5.0 mm.

5. The optical detection system of claim 1, wherein the light source is a light-emitting diode, the light permeable test paper comprises a coloration material, and at least a wavelength of the light-emitting diode is an absorption wavelength of the coloration material.

6. The optical detection system of claim 1, wherein the light source, the first aperture, the second aperture and the photo sensor together form an optical detection path, and the optical detection path is substantially perpendicular to the test strip.

7. The optical detection system of claim 1, further comprising:
   a strip moving carrier for fixing the test strip and linearly moving the test strip along a long axis of the first window, and the light beam irradiates a part of the cassette and the first window along the long axis.

8. The optical detection system of claim 7, wherein the strip moving carrier is an auto driving device or a manual driving device.

9. The optical detection system of claim 8, wherein the auto driving device is driven by a motor configured with a gear module.

10. The optical detection system of claim 9, wherein the gearing module comprises a sliding track, a screw rod, a gearwheel or a belt.

11. The optical detection system of claim 8, wherein the manual driving device comprises a sliding bulk and a sliding slot for linearly moving the test strip by hands or springs.

12. The optical detection system of claim 1, further comprising a signal analyzing module, wherein the signal analyzing module comprises:
   a signal analyzing unit receiving the measurement signal and retrieving a parameter from the measurement signal, wherein the parameter is a background signal parameter, a control signal parameter, a test signal parameter, or a first window time parameter; and
   a signal computing unit computing a concentration of a specific substance in a given sample based on at least one of the parameters.

13. The optical detection system of claim 1, wherein the optical detection system measures a detection signal hidden in fibers of the light permeable test paper through a transmission optical detection path.

14. The optical detection system of claim 1, wherein a diameter of the second aperture is less than the diameter of the first aperture so as to filter away redundant noise as the photo sensor receives the light beam.

15. The optical detection system of claim 1, wherein a diameter of the second aperture is less than or equal to the diameter of the first aperture.

\* \* \* \* \*